United States Patent
Benner et al.

(10) Patent No.: US 9,883,793 B2
(45) Date of Patent: Feb. 6, 2018

(54) SPATIAL MODELING OF VISUAL FIELDS

(71) Applicant: The Schepens Eye Research Institute, Inc., Boston, MA (US)

(72) Inventors: Philipp Benner, Boston, MA (US); Tobias Elze, Boston, MA (US); Peter Bex, Boston, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 71 days.

(21) Appl. No.: 14/913,576

(22) PCT Filed: Aug. 22, 2014

(86) PCT No.: PCT/US2014/052414
§ 371 (c)(1),
(2) Date: Feb. 22, 2016

(87) PCT Pub. No.: WO2015/027225
PCT Pub. Date: Feb. 26, 2015

(65) Prior Publication Data
US 2017/0258316 A1   Sep. 14, 2017

Related U.S. Application Data (60) Provisional application No. 61/869,627, filed on Aug. 23, 2013.

(51) Int. Cl.
*A61B 3/02* (2006.01)
*A61B 3/00* (2006.01)
*A61B 3/024* (2006.01)

(52) U.S. Cl.
CPC ............ *A61B 3/0025* (2013.01); *A61B 3/024* (2013.01)

(58) Field of Classification Search
USPC .................................................. 351/200–246
See application file for complete search history.

(56) References Cited

U.S. PATENT DOCUMENTS

| | | |
|---|---|---|
| 5,175,755 A | 12/1992 | Kumakhov |
| 5,192,869 A | 3/1993 | Kumakhov |
| 5,497,008 A | 3/1996 | Kumakhov |

(Continued)

FOREIGN PATENT DOCUMENTS

| | | |
|---|---|---|
| WO | WO-2009111454 A1 | 9/2009 |

OTHER PUBLICATIONS

Artes et al., Properties of perimetric threshold estimates from full threshold, SITA standard, and SITA fast strategies. Investigative Ophthalmology and Visual Science. 2002;43(8):2654-2659.

(Continued)

*Primary Examiner* — Mohammed Hasan
(74) *Attorney, Agent, or Firm* — Mintz Levin Cohn Ferris Glovsky and Popeo, P.C.; Ingrid A. Beattie (57) ABSTRACT

In some example implementations, there is provided a method. The method may include determining a probabilistic model representing threshold sensitivities across the visual field, the probabilistic model determined based on the data, the connection strengths, and the noise values. Related systems, methods, and articles of manufacture are also disclosed. In some implementations, the probabilistic model may include a continuous probability distribution.

15 Claims, 8 Drawing Sheets

(56) References Cited

U.S. PATENT DOCUMENTS

| | | |
|---|---|---|
| 5,570,408 A | 10/1996 | Gibson |
| 5,604,353 A | 2/1997 | Gibson et al. |
| 5,745,547 A | 4/1998 | Xiao |
| 6,285,506 B1 | 9/2001 | Chen |
| 6,317,483 B1 | 11/2001 | Chen |
| 6,527,391 B1* | 3/2003 | Heijl .................. A61B 3/024 351/243 |
| 6,934,359 B2 | 8/2005 | Chen et al. |
| 7,035,374 B2 | 4/2006 | Chen |
| 7,072,439 B2 | 7/2006 | Radley et al. |
| 7,110,506 B2 | 9/2006 | Radley et al. |
| 7,209,545 B2 | 4/2007 | Radley et al. |
| 7,257,193 B2 | 8/2007 | Radley et al. |
| 7,729,471 B2 | 6/2010 | Burdett, Jr. et al. |
| 7,738,629 B2 | 6/2010 | Chen |
| 8,233,715 B2* | 7/2012 | Matsushita .......... G06K 9/00 348/241 |
| 2010/0007851 A1* | 1/2010 | Lu ...................... A61B 3/022 351/242 |
| 2011/0170666 A1 | 7/2011 | Chen et al. |
| 2011/0190657 A1 | 8/2011 | Zhou et al. |
| 2013/0201452 A1* | 8/2013 | Crabb .................. A61B 3/024 351/224 |

OTHER PUBLICATIONS

Aulhorn et al., Frequency distribution in early glaucomatous visual field defects. Documenta Ophthalmologist. Proceedings Series. 1977;14:75-83.

Betz-Stablein et al., Spatial Modeling of Visual Field Data for Assessing Glaucoma Progression. Investigative Ophthalmology and Visual Science. 2013;54(2):1544-53.

Keltner et al., Classification of visual field abnormalities in the ocular hypertension treatment study. Archives of Ophthalmology. 2003;121(5):643-650.

Rasmussen et al., Gaussian Processes for Machine Learning. MIT Press. (2006). <www.gaussianprocess.org/gpml/chapters/>.

* cited by examiner

SPATIAL MODELING OF VISUAL FIELDS

CROSS-REFERENCE TO RELATED APPLICATIONS

The current application is a national stage application, filed under 35 U.S.C. § 371, of International Application No. PCT/US2014/052414, filed on Aug. 22, 2014, which claims benefit of priority under 35 U.S.C. § 119(e) to U.S. Provisional Patent Application No. 61/869,627 filed on Aug. 23, 2013, entitled "Spatial Modeling of Visual Fields," the contents of which are incorporated herein by reference in their entirety for all purposes.

TECHNICAL FIELD

The subject matter described herein relates generally to modeling visual fields for use in medical diagnosis.

BACKGROUND

Visual fields are a spatial array of visual sensitivity. Visual fields are frequently assessed in vision research and in ophthalmology to determine vision loss and to diagnose diseases such as glaucoma and the like. For example, an ophthalmic perimeter (also referred to as a visual field perimeter) is a test device that can be used for these measurements. The ophthalmic perimeter typically returns sensitivity values for a set of isolated visual field locations. The minimum luminance required for the patient to detect the illumination is called the threshold sensitivity of that location. The reliability of each measurement may be estimated by global indices, such as the proportion of incorrect answers given by the patient during a complete perimetry exam.

SUMMARY

In one aspect there is provided a method. The method may include obtaining data representative of a population of patients. The data may include visual threshold sensitivity information as a function of location within a visual field. The method may also include determining connection strengths between points within the visual field using the data and a connection strength model. The method may further include determining noise measures across the visual field from the data and a noise measure model. Based on the data, the connection strengths, and the noise measures, a probabilistic model may be determined that represents the threshold sensitivities of the population of patients across the visual field.

In some variations, one or more of the features disclosed herein including the following features can optionally be included in any feasible combination. In some implementations, the probabilistic model may include a continuous probability distribution. In some implementations, the continuous probability distribution may be a Gaussian distribution. In some implementations, the determining the probabilistic model may further be based on visual field data from a patient being tested. In some implementations, the determined probabilistic model may be compared to one or more known models corresponding to one or more specific diseases.

DETAILED DESCRIPTION

Visual field testing of patients may be performed for use in vision research and in ophthalmology for the diagnosis of diseases. Visual field testing determines visual functions over a spatial array where humans or animals are visually sensitive. Visual field testing can be performed by a variety of devices including ophthalmic perimeters. The ophthalmic perimeter may be used to measure a patient's threshold visual sensitivity for one or more visual field locations. The ophthalmic perimeter may measure a visual field by having a patient look or stare at a fixed point in the ophthalmic perimeter, while the ophthalmic perimeter successively illuminates discrete visual field locations. Meanwhile, the patient may be instructed to press a button (or respond in some way) each time the patient sees the illumination. Although the ophthalmic perimeter can be effective, ophthalmic perimeters may be configured to measure visual field locations without using information about other nearby visual field locations—thus ignoring the spatial structure of the visual field.

In some example implementations, there may be provided a method that includes using a probabilistic model. This probabilistic model may represent an expected measure of visual ability, such as threshold sensitivity, as a function of location in the visual field.

In some example implementations, the probabilistic model (also referred to herein as the model) may be used to adjust visual function testing, such as perimetry, and this adjustment may be performed during actual testing process of a patient. While a patient is undergoing visual function testing using for example an ophthalmic perimeter, the configuration of the visual function testing may be adjusted based on the patient's responses during the testing, as the model returns not only an estimate of visual function but also an estimate of its credibility over all locations in the visual field. For example, if the probabilistic model suggests that a particular area of the visual field is less credible than other areas, then additional visual function testing in that area may provide a more accurate characterization of the patient's visual field in that area and overall. In another example, if another particular area tends to be highly credible, then fewer visual function testing locations may be used, reducing the overall time of the testing. The resulting visual function test outcome may provide a more precise mapping of visual fields and a higher confidence in the results.

Figure 1:
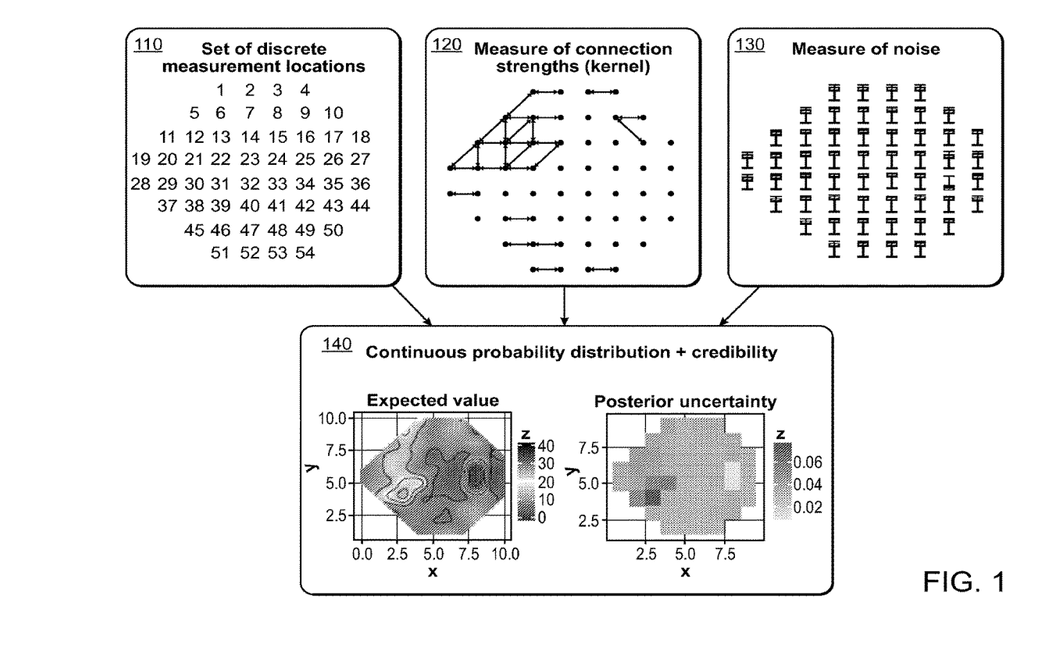
FIG. 1 depicts an example of a continuous probability distribution representing visual threshold sensitivity and credibility estimates, in accordance with some example implementations.

FIG. 1 depicts an example of a process for generating a probabilistic model, such as a continuous probability distribution and the like, representing a visual ability/function of a patient across a visual field using a single visual field measurement.

At 110, data from a patient is received at a processor, such as a computer, central processing unit, and/or the like. This data consists of numeric values representing visual function, such as visual sensitivity, at a set of discrete measurement locations within the visual field. For example, one or more ophthalmic perimeter devices may measure visual sensitivity at one or more locations of the visual field of a patient/subject. These visual field measurements may be collected and provided as data at 110. Moreover, simulated patient data and/or animal data may be used at 110 as well.

At 120, a pre-defined kernel $k(x1,x2)$ which represents the connection strength between any two visual field locations x1 and x2. The kernel can reflect a global measure of connectivity regardless of the location within the visual field, but may also be dependent on location. This location specificity can be based, for example, on prior knowledge about the spatial structure of visual function, on physiological structures known to have an impact on visual function, or it can be empirically derived from patient measurements. This location specificity can either be represented by an inhomogeneous kernel or, as in some example implementations, by a homogeneous kernel which operates on the visual field locations which are shifted in such a way that their relative distances reflect their connectivities. In some example implementations, the kernel may be a Gaussian function as described with respect to FIG. 5, although other kernel functions may be used as well. If the kernel includes connection strengths that depend on location, this location dependence may vary for different diseases. Diseases such as glaucoma are known to have specific spatial structures of visual field loss. The choice of the kernel can be fixed prior to the measurement based on a disease expectation, or the choice of the kernel can be dynamically adapted during the measurement. For example, a kernel may be adapted during the measurement of a patient based on the measurement. A determination of likely diseases based on the measurement may also be determined.

At 130, the model may use a noise estimate at each of the measurement locations. This noise estimate can be the same for each location or vary by location. In some example implementations, the noise estimate has been derived from patient populations by analyzing the distribution of their measurement values over repeated measurements. The measure of the noise may include a mean (which may have a value of zero) and/or a variance. The distribution of the noise may be a Gaussian distribution, although other distributions may be used as well.

At 140, the processor may determine the probabilistic model, such as the continuous probability distribution, relating the positions in the visual field with visual function measurements, such as threshold visual sensitivities, based on the received data (110), the kernel (120), and noise estimates (130). Although patient population data may have been taken at discrete locations in the patient's visual fields, the continuous probability distribution determined at 140, acts as a prediction of visual function at any location of the visual field, independent of the locations the patient has been measured or, whether the patient has been measured at all.

In the example depicted at 140, the continuous probability distribution including the expected values are plotted for an example data set. Specifically, the expected value $\mathbb{E}[f^*|x^*, y, x]$ is used to represent the expected threshold sensitivity values at locations x* given a set of measurements y at locations x. This expected value shown at 140 is based on a spatial layout of a visual field test of a Humphrey Field Analyzer (HFA), although other types of perimeter devices may be used as well. The credibility of each measurement point (also referred to as certainty) is also determined at 140 as shown for the visual field locations in the patient population data. The credibility is defined as the entropy of the posterior distribution at a set of locations x*. In some example implementations, the certainty information is used to adapt measurements taken during patient testing. For example, testing at visual field locations with high uncertainty could be enhanced with additional nearby testing locations in order to balance the uncertainty across the visual field of the perimeter test. In some example implementations, also the posterior expectation is used to adapt measurements.

In some example implementations, the model can be applied separately to different parts of the visual field in order to test one or more hypotheses. For example, glaucoma may be tested by comparing upper and lower visual hemifield as separate probability distributions.

Figure 2:
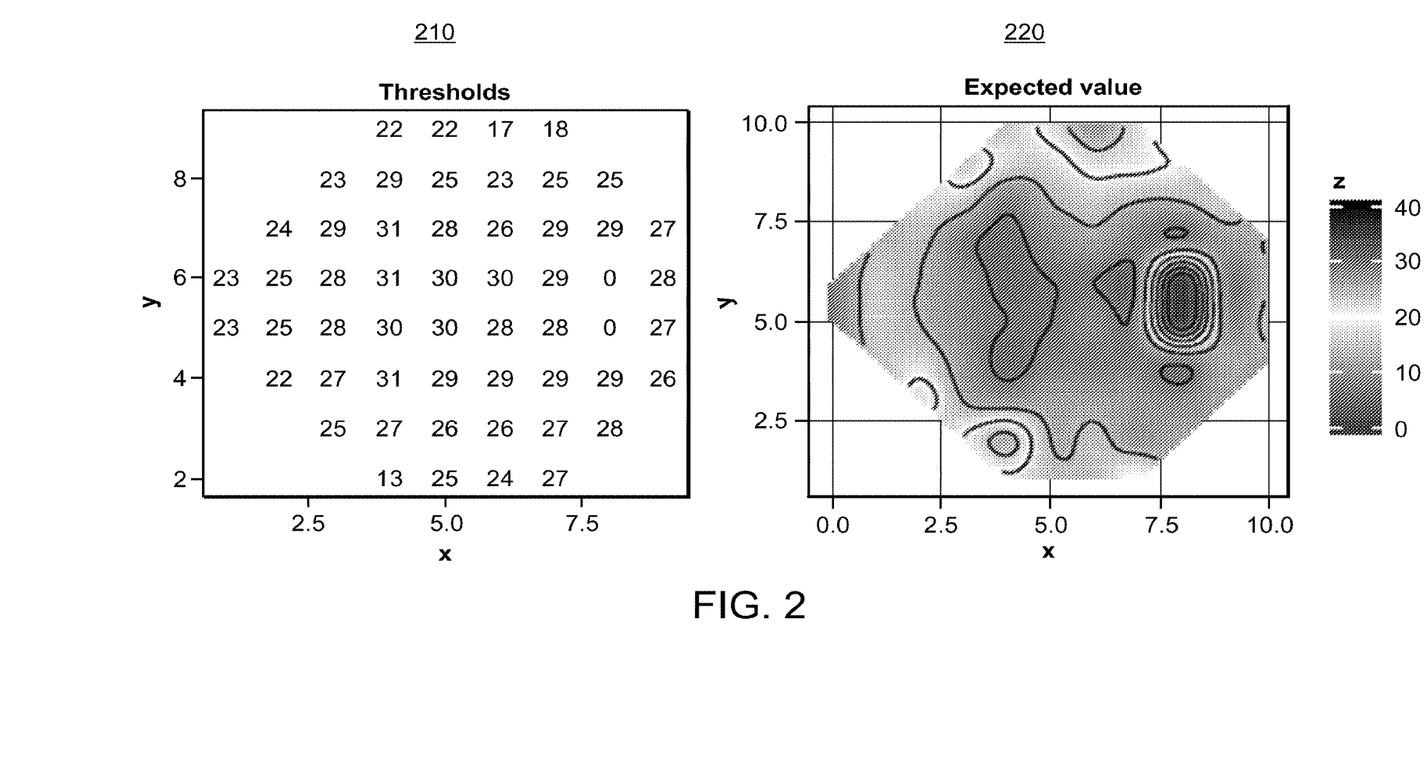
FIG. 2 depicts an example of the threshold sensitivity of a patient at a set of discrete locations and the expected values of a continuous probability distribution, in accordance with some example implementations.

FIG. 2 depicts example data. The plot at 210 depicts thresholds measured with a perimeter such as a Humphrey Field Analyzer (HFA) on a single patient. At 220, the plot shows the expected value of threshold sensitivity computed on the threshold data at 210.

Referring again to 210, a perimeter, such as a Humphrey Field Analyzer, may be used to make the patient measurements. The tested discrete locations of different patients may correspond to different locations due to the perimeter used. For example, different manufacturers and different models from a single manufacturer may test different visual field locations.

The plot at 220 shows the expected value of threshold sensitivity for a single patient. Specifically, the plot shows the expected value of threshold given data from a single patient, an exponential kernel representing the connection strengths, and Gaussian noise. The expected value and the exponential kernel are further described below with respect to FIG. 5.

Figure 3:
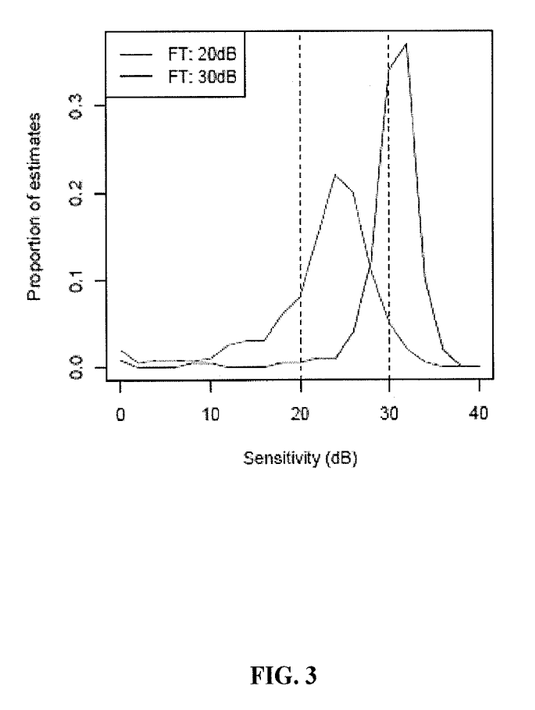
FIG. 3 depicts an example of the variability of the threshold sensitivity of four patients over multiple perimetry tests, in accordance with some example implementations.

FIG. 3 shows an example plot of the variability of the threshold sensitivity of four patients over multiple perimetry tests. FIG. 3 shows the test—retest variability of the Humphrey Field Analyzer (HFA) Swedish Interactive Threshold Algorithm (SITA) standard (SS 24-2) method. A Full Threshold (FT 24-2) measurement taken during the same test session was used as a baseline reference. In the example of FIG. 3, the dispersion of the distribution varies with its mean (heteroscedasticity). In other words, the lower the mean threshold, the larger is the variability. Also seen in the example of FIG. 3 is that the negative skew of the distribution increases with decreasing mean.

Figure 4:
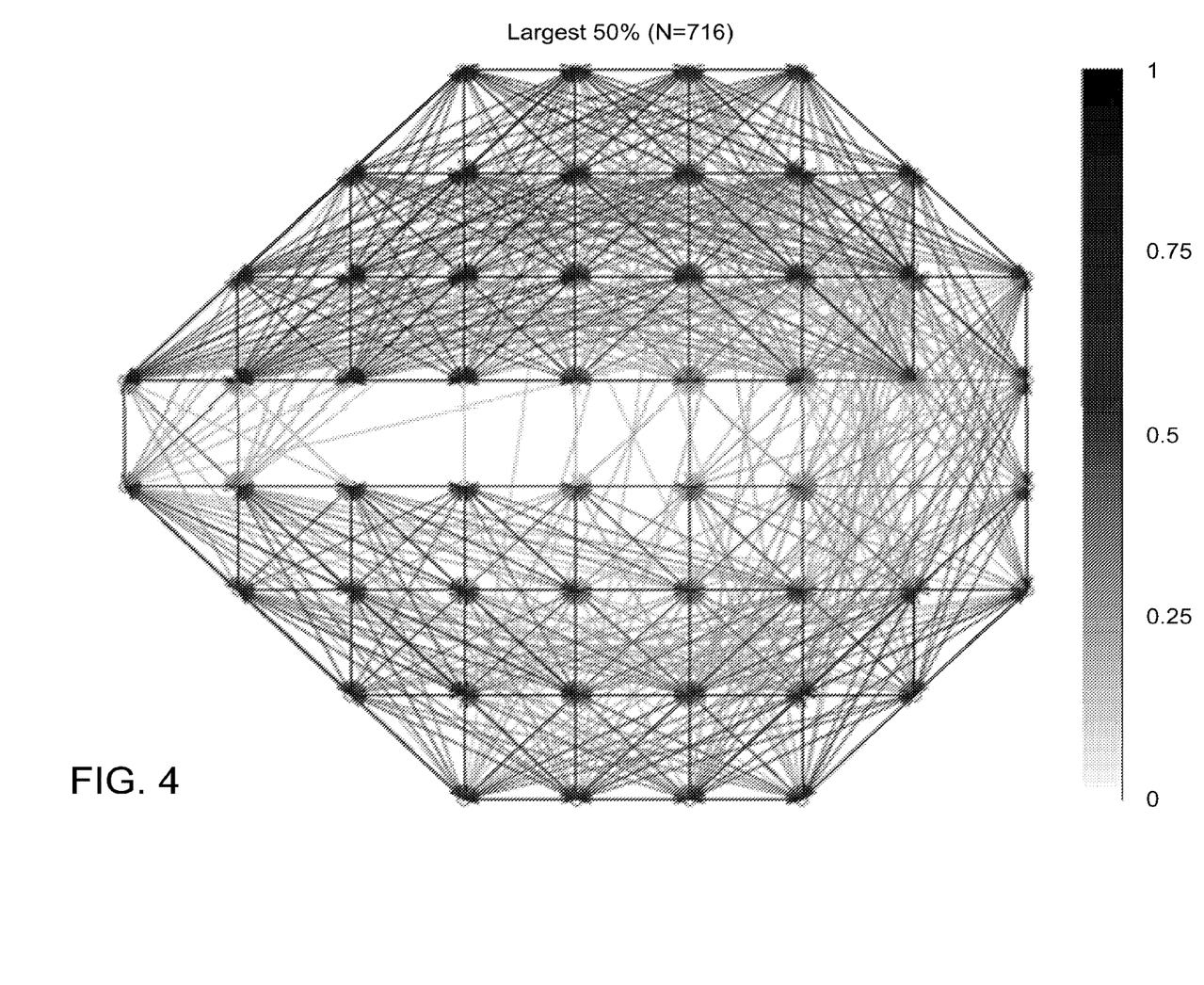
FIG. 4 depicts an example of a pattern of connection strengths from a set of glaucoma patients, in accordance with some example implementations.

FIG. 4 depicts an example pattern of connection strengths from a set of patients with suspected glaucoma, although other types of patient data may be used as well including healthy patients. A connection strength pattern is sometimes referred to as a correlation structure. Patterns indicating different diseases may be determined by ophthalmological knowledge or by patterns from patients or populations of patients that have a particular disease. FIG. 4 shows the 50% strongest correlations from a set of glaucoma patients. This data may be used to determine the parameters of the statistical model that control the connection strength between measurement locations, i.e. the parameters of the kernel function or relative distance between measurement locations.

Figure 5:
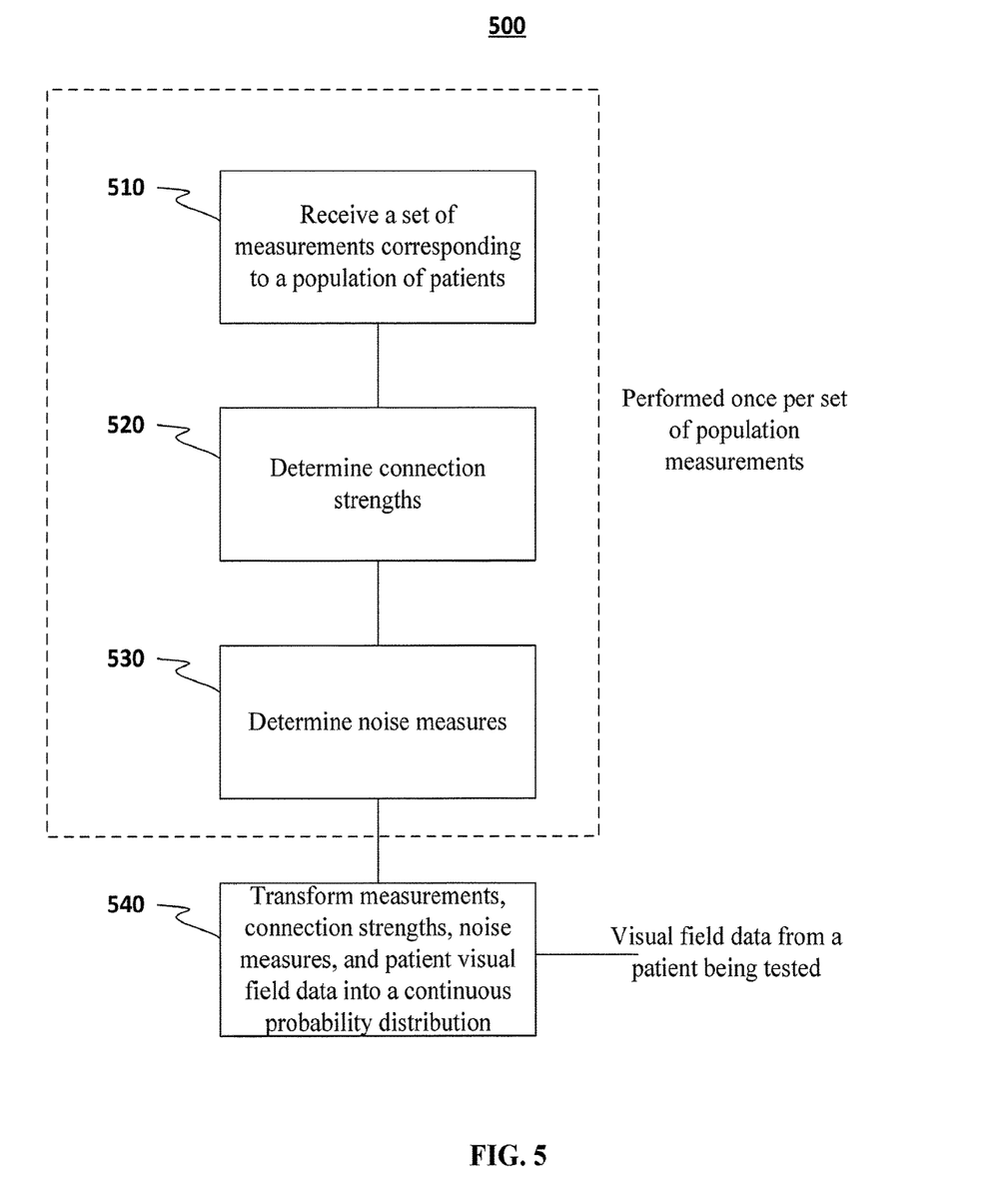
FIG. 5 depicts an example of a process for determining a continuous probability distribution of visual threshold sensitivity across a visual field, in accordance with some example implementations.

FIG. 5 depicts an example of a process 500 for determining the parameters of the probabilistic model of threshold sensitivity across a visual field. The description of FIG. 5 also refers to FIG. 1.

At 510, a processor may receive patient/subject data as described above with respect to FIG. 1 at 110.

At 520, a processor may determine the connection strengths between different measurement locations. The connection strengths between different locations in the visual field are represented by a kernel function which may take the following form:

$$k(x_p, x_q) = \sigma_f^2 \exp\left\{-\frac{1}{2l^2} d(x_p, x_q)^2\right\},\qquad \text{Equation 1}$$

wherein
$k(x_p, x_q)$ is a Gaussian kernel function,
$x_p$ and $x_q$ represent locations in the visual field,
$\sigma_f^2$ denotes the kernel variance,
exp denotes the natural exponential function,
l is a length scale, and
the distance between two locations, $x_p$ and $x_q$, may be represented by the following:

$$d(x_p, x_q)\qquad \text{Equation 2},$$

wherein locations $x_p$ and $x_q$ may be locations on a planar surface, or locations on the surface of a sphere.

A kernel consistent with Equations 1 and 2 may have an exponential decay of the covariance with increasing distance, although other types of kernel functions may also be used.

The connection strength between any two points in a visual field, such as $x_p$ and $x_q$, may depend on the distance between the two points no matter the position of the points within the visual field. So, two points a certain distance apart in one area of the visual field would have the same connection strength as two different points in another part of the visual field that are the same distance apart.

Each physical measurement location in the perimeter is identified with a location in the statistical model. In some example implementations, the distance between two points x and y in the statistical model may not match the actual physical distance, but rather the correlation strength that was determined from the population of patients. For example, if the correlation between two points x and y is weaker in the population data than in the model, moving the measurement locations of the statistical model farther apart from one another decreases the connection strength. In this way, the measurement locations may be shifted so that the correlations between adjacent points in the field have the same or nearly the same value. This may also be achieved by maximizing the marginal likelihood of the statistical model on the population data with respect to the measurement locations of the model.

At 530, a processor may calculate the noise at each of the measurement locations in the data received at 510. For example, the data may include patient population data corresponding to a particular location in the visual field that may be used to determine the noise at that location in the visual field. The measure of the noise may include a mean (which may have a value of about zero) and a variance. The noise may also have a distribution, such as a Gaussian distribution, although other distributions including a Raleigh distribution may be used as well. 510-530 are performed once per set of measurements corresponding to a population of patients.

At 540, a processor may determine the parameters of the probabilistic model, based on the set of measurements corresponding to a population of patients 510, connection strengths 520, noise measures 530, and visual field from a patient being tested 550. The probabilistic model, such as the continuous probability distribution, provides an expected threshold sensitivity at any location in the visual field not just the visual field locations in the received data. The expected value $\mathbb{E}[f^* | x^*, y, x]$ represents the posterior expected threshold sensitivity values at locations $x^*$ given a set of measurements y at locations x.

In some example implementations, a processor determines the probabilistic model in the form of a continuous probability distribution. For example, a processor starting with two locations x1 and x2 on the visual field and their associated sensitivities f1 and f2, if f1 is determined, then f2 is normally distributed with mean and variance depending on f1 and the distance between x1 and x2. For example, if x1 and x2 are moved closer together, the mean of the distribution of f2 may move closer to f1, and the variance of the distribution may decrease. The joint distribution may be represented by the following equation:

$$p(f_1, f_2 | x_1, x_2) = p(f_1 | x_1) p(f_2 | f_1, x_1, x_2)\qquad \text{Equation 3.}$$

In some example implementations, when the distribution of f1 given x1 is Gaussian, then f1, f2, given x1, x2 jointly follow a normal distribution. In these implementations, the covariance matrix of this joint distribution represents the spatial correlations.

The posterior threshold sensitivity is a distribution of threshold sensitivities that may be evaluated by a processor at any finite set of locations. The distribution is defined by a likelihood model and the prior distribution. The prior distribution is a Gaussian process which can be understood as an infinite dimensional Gaussian distribution. Each finite set of threshold sensitivities $f = \{f_1, f_2, \ldots, f_n\}$ at locations $x = \{x_1, x_2, \ldots, x_4\}$ is a priori distributed as:

$$f | x \sim N(\mu_0, k(x, x)),\qquad \text{Equation 4,}$$

wherein
$\mu_0$ is the a priori mean, and
$k(x, x)$ the covariance matrix evaluated at locations $x_1, x_2$, and so forth to $x_n$.

Given a sensitivity measurement yi at location xi, the value of the sensitivity fi may satisfy the following equation:

$$y_i = f_i + \epsilon\qquad \text{Equation 5,}$$

wherein
$\epsilon$ is independent and identically distributed and may in some implementations be Gaussian noise with zero mean and variance $\sigma_n^2$. This defines the likelihood model.

To predict the sensitivity at a set of locations $x^*$ given a set of measurements y at locations x, the posterior expectation may be used and is represented by the following equation:

$$\mathbb{E}[f^* | x^*, y, x]\qquad \text{Equation 6.}$$

The values $x^*$ and x may correspond to two sets of locations, which may be different. Moreover, a prediction of sensitivity may be determined by the processor at locations where there are no corresponding measurements in the data received at 510.

The parameters of the prior distribution and kernel function may be determined by utilizing threshold sensitivity data from a data set (such as a population of patients and the like) and correlations between measurement locations. A measure of noise determined from the data set may be utilized to fix the parameters of the likelihood model.

The probabilistic model, generated at 540, may be used in a variety of ways. For example, perimetry test results from a given patient may be compared to probabilistic model/continuous probability distribution to assess the condition of the patient as described further below with respect to FIG. 6B.

For a given visual field measurement M, the process (e.g., process 500) may be used to calculate the probabilities for hypotheses about the data from a particular patient and determine which of the hypotheses is most likely true. The hypotheses may come from a research questions or from clinical requirements. The hypotheses may correspond to the patient having one or more diseases. Based on the above-noted model, the likelihood of M given that any hypothesis H is true (p(M|H)) can be calculated. In the case of several hypotheses H1 to Hn, one can compare the likelihoods of M given each of hypotheses H1 to Hn. In some example implementations, if there are two hypotheses, such as the hypothesis that a patient is healthy, H1, or has a disease, H2, the ratio of these two likelihoods is used to determine which hypothesis, H1 or H2, is most likely true. For example, which hypothesis is more likely to be true may be determined by a processor using the Bayes Factor B. The Bayes Factor has an established interpretation for statistical inference, which can be expressed with respect to the foregoing example as: For B<⅓ substantial evidence for the healthiness hypothesis exists, for ⅓<B<3, no satisfyingly definite conclusion can be made that M is healthy or not, and for B>3, substantial evidence for the disease hypothesis exists. Note that there are different proposals for decision criteria than ⅓ and 3 which can also be applied. The Bayes Factor, or other decision measures based on probabilities, may be used as a basis for evaluating competing disease hypothesis in computer based diagnostic testing.

The diagnosis of a progression of visual field loss requires a distance measure between visual field measurements or distributions of measurements as described in the foregoing. The Kullback-Leibler (KL) divergence provides a measure for the distance between distributions. Other possible measures may also be used.

Figure 6A:
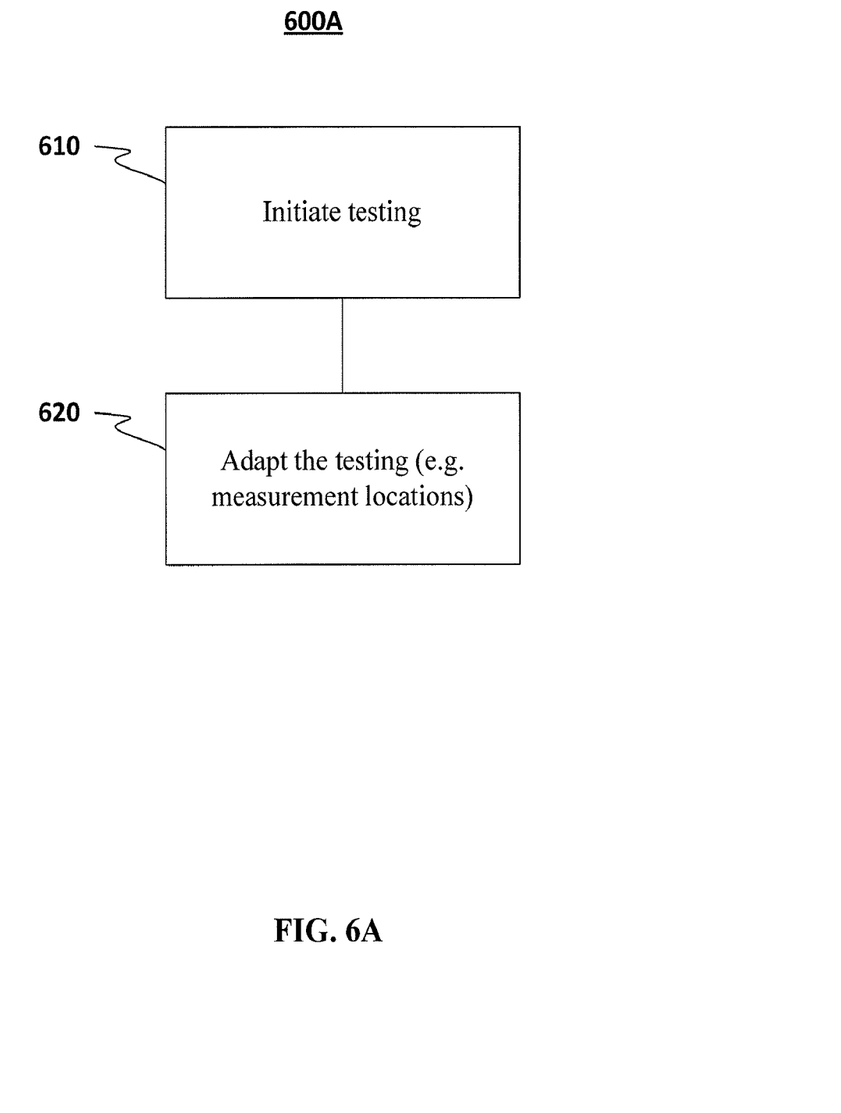
FIG. 6A depicts an example of a process for adapting the testing of a patient while the testing is being performed, in accordance with some example implementations

FIG. 6A depicts a process 600A for adapting the testing of a patient while the testing is being performed. At 610, testing may be initiated based on a probabilistic model, such as the model determined at 140 or 540. At 620, the adapting may include adapting the location of successive measurements to improve confidence in a diagnosis and/or repeating the measurement of previously measured locations. The adapting may be performed based on the probabilistic model and/or the patient's responses. For example, in an area with low credibility according to the probabilistic model, additional testing locations in that area may improve the confidence of the test results. The adapting may also be performed based on the patient's responses. For example, if the patient's responses are unlikely to reflect the true underlying visual function in a particular area of the visual field, additional testing points or re-testing of previous locations may be performed to better map the patient's visual field. In this way, the visual function test may be adapted to improve the reliability of diagnoses.

Figure 6B:
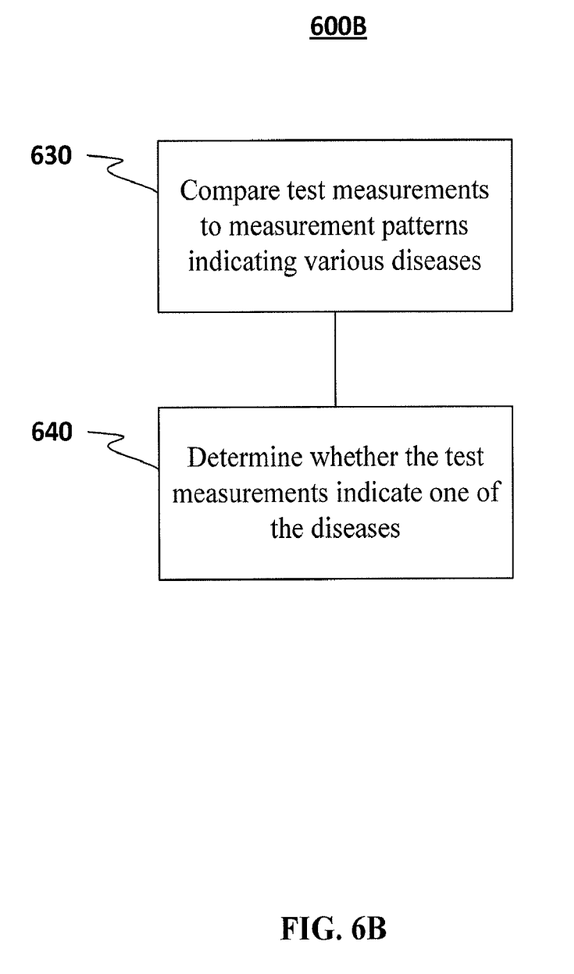
FIG. 6B depicts an example of a process for identifying patients with various diseases, in accordance with some example implementations.

FIG. 6B depicts a process 600B performed by a processor for identifying patients with various disorders/diseases. At 630, test results from a patient's measurements may be compared to patterns that have been identified as indicating the disorders/diseases. The patterns may be determined from data from patients that have the disorder/disease, although other types of subjects can be used as well. The patterns may also be determined from a probabilistic model (e.g., the model determined at 140 or 540) representing data corresponding to one or more subjects with the disorder/disease.

To illustrate further, in some example implementations, the probabilistic model/continuous probability distribution of a measurement of a patient may be compared to the probabilistic models of normal subjects at 510 (subjects/patients having normal visual sensitivities) in order to assess whether the patient's results differ from normality. In some example implementations, the same type of comparison can be performed to probabilistic models of subjects/patients having specific visual disorder (for example, glaucoma, and the like). When this is the case, perimetry test results from a given patient may be compared to probabilistic model/continuous probability distribution to assess, at 640, whether the patient's results indicate the specific visual disorder.

Figure 7:
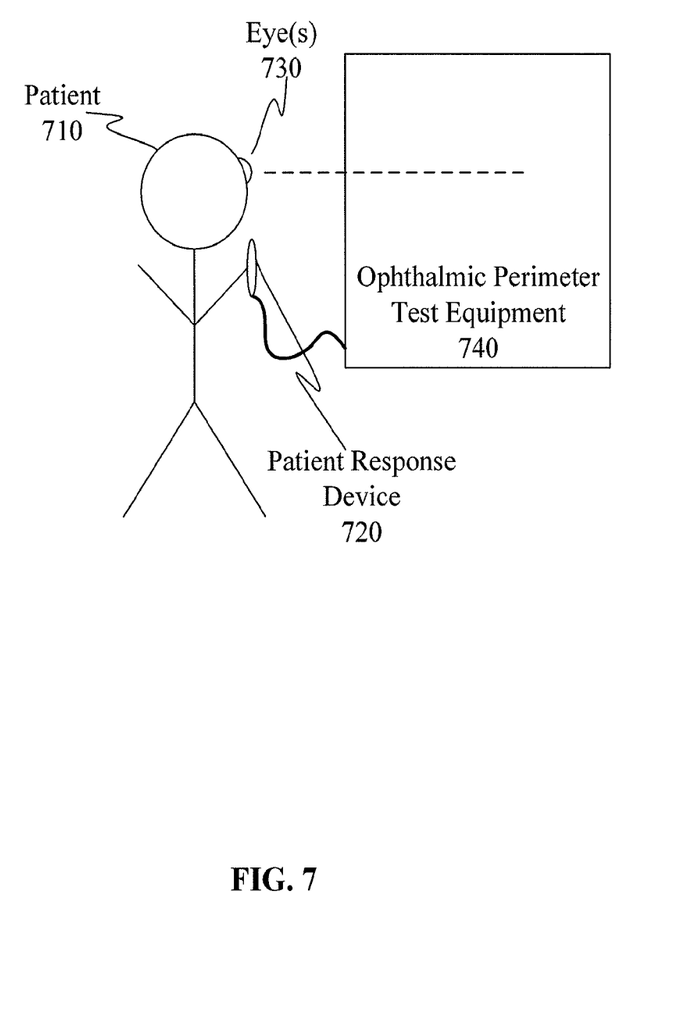
FIG. 7 depicts a patient being tested using ophthalmic perimeter test equipment, in accordance with some example implementations.

FIG. 7 depicts a patient being tested using ophthalmic visual function test equipment 740 (e.g., perimeter). A patient 710 being tested looks or stares into the perimeter 740. The patient 710 fixes their eyes 730 in one direction. When the test is initiated, a processor in the perimeter determines the first of one or more locations inside the perimeter 740 to illuminate. When the patient sees the illuminated location inside the perimeter, the patient presses the patient response device connected to the perimeter. The illuminated locations inside the perimeter are presented so that the patient does not know a priori when or where the illumination will be presented. This can reduce false responses by the patient. Based on the probabilistic model being used and the patient's responses, the perimeter testing may be adapted as described at 600A to provide better diagnoses.

Although the foregoing description includes a perimeter performing the measurements, other diagnostic equipment may be used instead. Although disorders/diseases of the eye are described above, other diseases may be identified using the same or similar process. Some disorders/diseases may not require diagnostic test equipment for measurements. The probabilistic model may be determined using any computing device that includes a processor.

One or more aspects or features of the subject matter described herein can be implemented in a processor. A processor may include digital electronic circuitry, integrated circuitry, specially designed application specific integrated circuits (ASICs), field programmable gate arrays (FPGAs), computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method comprising:
    receiving data that includes visual threshold sensitivity information as a function of location within a visual field;
    determining, from the data and a connection strength model, connection strengths between points within the visual field;
    determining, from the data and a noise measure model, noise values across the visual field; and
    determining a probabilistic model representing threshold sensitivities across the visual field, the probabilistic model determined based on the data, the connection strengths, and the noise values.

2. The method of claim 1, wherein the probabilistic model is a continuous probability distribution.

3. The method of claim 2, wherein the continuous probability distribution is Gaussian.

4. The method of claim 1, wherein the determining the probabilistic model is further based on visual field data from a patient being tested.

5. The method of claim 4, wherein the determined probabilistic model is compared to one or more known models corresponding to one or more specific diseases.

6. An apparatus comprising:
    at least one processor; and
    at least one memory including computer program code, the at least one processor, the at least one memory, and the computer program code configured to cause the apparatus to at least:
    receive data that includes visual threshold sensitivity information as a function of location within a visual field;
    determine, from the data and a connection strength model, connection strengths between points within the visual field;
    determine, from the data and a noise measure model, noise values across the visual field; and
    determine a probabilistic model representing threshold sensitivities across the visual field, the probabilistic model determined based on the data, the connection strengths, and the noise values.

7. The apparatus of claim 6, wherein the probabilistic model is a continuous probability distribution.

8. The apparatus of claim 7, wherein the continuous probability distribution is Gaussian.

9. The apparatus of claim 6, wherein the determining the probabilistic model is further based on visual field data from a patient being tested.

10. The apparatus of claim 9, wherein the determined probabilistic model is compared to one or more known models corresponding to one or more specific diseases.

11. A non-transitory computer-readable medium encoded with instructions that, when executed by at least one processor, cause operations comprising:
    receiving data that includes visual threshold sensitivity information as a function of location within a visual field;
    determining, from the data and a connection strength model, connection strengths between points within the visual field;
    determining, from the data and a noise measure model, noise values across the visual field; and
    determining a probabilistic model representing threshold sensitivities across the visual field, the probabilistic model determined based on the data, the connection strengths, and the noise values.

12. The non-transitory computer-readable medium of claim 11, wherein the probabilistic model is a continuous probability distribution.

13. The non-transitory computer-readable medium of claim 12, wherein the continuous probability distribution is Gaussian.

14. The non-transitory computer-readable medium of claim 11, wherein the determining the probabilistic model is further based on visual field data from a patient being tested.

15. The non-transitory computer-readable medium of claim 14, wherein the determined probabilistic model is compared to one or more known models corresponding to one or more specific diseases.

* * * * *